US007008454B2

(12) United States Patent
Fenning et al.

(10) Patent No.: US 7,008,454 B2
(45) Date of Patent: Mar. 7, 2006

(54) PROSTHETIC KNEE WITH REMOVABLE STOP PIN FOR LIMITING ANTERIOR SLIDING MOVEMENT OF BEARING

(75) Inventors: John B. Fenning, Fort Meyers, FL (US); Michael J. Pappas, Jensen Beach, FL (US)

(73) Assignee: Biomedical Engineering Trust I, South Orange, NJ (US)

( * ) Notice: Subject to any disclaimer, the term of this patent is extended or adjusted under 35 U.S.C. 154(b) by 69 days.

(21) Appl. No.: 10/670,104

(22) Filed: Sep. 24, 2003

(65) Prior Publication Data
US 2004/0204765 A1  Oct. 14, 2004

Related U.S. Application Data

(63) Continuation-in-part of application No. 10/410,779, filed on Apr. 9, 2003.

(51) Int. Cl.
*A61F 2/38*  (2006.01)
(52) U.S. Cl. .................................. 623/20.29
(58) Field of Classification Search ....... 623/20.14–15, 623/20.21–25, 20.27–32, 20.34
See application file for complete search history.

(56) References Cited

U.S. PATENT DOCUMENTS

| 4,001,896 | A |  | 1/1977 | Arkangel |
| 4,007,495 | A |  | 2/1977 | Frazier |
| 4,219,893 | A |  | 9/1980 | Noiles |
| 4,224,697 | A |  | 9/1980 | Murray et al. |
| 4,309,778 | A |  | 1/1982 | Buechel et al. |
| 4,340,978 | A |  | 7/1982 | Buechel et al. |
| 4,353,136 | A |  | 10/1982 | Polyzoides et al. |
| 4,470,158 | A |  | 9/1984 | Pappas et al. |
| 4,673,408 | A | * | 6/1987 | Grobbelaar ............... 623/20.29 |
| 4,728,332 | A |  | 3/1988 | Albrektsson |
| 4,834,081 | A | * | 5/1989 | Van Zile ...................... 606/99 |
| 4,950,297 | A |  | 8/1990 | Elloy et al. |
| 5,007,933 | A |  | 4/1991 | Sidebotham et al. |
| 5,194,066 | A | * | 3/1993 | Van Zile .................. 623/20.15 |
| 5,370,701 | A |  | 12/1994 | Finn |
| 5,395,401 | A |  | 3/1995 | Bahler |
| 5,702,466 | A |  | 12/1997 | Pappas et al. |
| 6,080,195 | A |  | 6/2000 | Colleran et al. |
| 6,210,443 | B1 | * | 4/2001 | Marceaux et al. ........ 623/20.33 |
| 6,217,618 | B1 | * | 4/2001 | Hileman .................. 623/20.33 |
| 6,238,434 | B1 |  | 5/2001 | Pappas |
| 6,319,283 | B1 |  | 11/2001 | Insall et al. |
| 6,458,160 | B1 |  | 10/2002 | Biegun et al. |

(Continued)

FOREIGN PATENT DOCUMENTS

DE      25 45 821        4/1976

(Continued)

*Primary Examiner*—Eduardo C. Robert
*Assistant Examiner*—Annette R. Reimers
(74) *Attorney, Agent, or Firm*—Gerald E. Hespos; Anthony J. Casella

(57) ABSTRACT

A knee prosthesis includes a femoral component, a tibial component, a bearing and a control arm. The bearing is in articular bearing engagement with the femoral component and in sliding and rotational bearing engagement with the tibial component. Movement of the bearing relative to the tibial component is controlled by a control arm. Anterior and posterior extremes of the control arm include stops for limiting anterior and posterior movement of the bearing relative to the tibial component. At least one of the stops is removable relative to the control arm to facilitate implantation.

9 Claims, 10 Drawing Sheets

U.S. PATENT DOCUMENTS

| | | | |
|---|---|---|---|
| 6,475,241 B1 * | 11/2002 | Pappas | 623/20.29 |
| 6,491,726 B1 | 12/2002 | Pappas | |
| 6,755,864 B1 | 6/2004 | Brack et al. | |
| 6,764,516 B1 * | 7/2004 | Pappas | 623/20.29 |
| 6,797,005 B1 * | 9/2004 | Pappas | 623/20.27 |
| 2001/0034555 A1 * | 10/2001 | Pappas | 623/20.29 |
| 2002/0156535 A1 * | 10/2002 | Pappas | 623/20.29 |
| 2003/0009229 A1 * | 1/2003 | Pappas | 623/20.27 |

FOREIGN PATENT DOCUMENTS

| | | |
|---|---|---|
| DE | 25 50 704 | 5/1976 |
| DE | 35 29 894 | 3/1987 |
| DE | 91 10 504.8 | 8/1991 |
| DE | 91 10 504.8 | 10/1991 |
| EP | 0 186 471 | 7/1986 |
| EP | 0 349 173 | 1/1990 |
| EP | 0 519 873 | 12/1992 |
| EP | 0 529 408 | 3/1993 |
| FR | 2 663 536 | 12/1991 |
| GB | 2 223 950 | 4/1990 |
| WO | WO 92/08424 | 5/1992 |
| WO | WO 96/08215 | 3/1996 |
| WO | WO 01/97719 A1 | 12/2001 |

* cited by examiner

PROSTHETIC KNEE WITH REMOVABLE STOP PIN FOR LIMITING ANTERIOR SLIDING MOVEMENT OF BEARING

This application is a continuation-in-part of U.S. patent application Ser. No. 10/410,779, filed Apr. 9, 2003.

BACKGROUND OF THE INVENTION

1. Field of the Invention

A prosthetic knee joint is provided with a femoral component, a tibial component and a bearing between the femoral and tibial components. The bearing is capable of rotational movement on the tibial component and anterior-posterior sliding movement on the tibial component in response to flexion of the knee.

2. Description of the Related Art

U.S. Pat. No. 5,702,466 shows a knee prosthesis with a tibial component that has a superior bearing surface. The prosthesis further includes a femoral component with an inferior articular bearing surface. A bearing is disposed between the tibial and femoral component and includes an inferior surface in rotating and sliding bearing engagement with the superior surface of the tibial component. The bearing further includes a superior surface in articular bearing contact with the inferior surface of the femoral component. Movement of the bearing on the tibial component is controlled by a control arm. More particularly, the bearing includes a groove that extends in an anterior-posterior direction in the inferior surface of the bearing. A control arm assembly is pivotally mounted to the tibial component and includes an arm that is slidably engaged in the groove of the bearing. Thus, the bearing and the control arm can rotate together on the superior surface of the tibial component. Additionally, the bearing can slide on the superior surface of the bearing and along the arm of the control arm assembly.

The ability of the tibia to move forward relative to the femur is critical in the achievement of maximum passive flexion. If the tibia does not so move its posterior aspect will impinge sooner against the posterior aspect of the femur, thereby limiting flexion sooner. Where the posterior cruciate is not salvageable, or viable, the posterior stabilized knee device shown in U.S. Pat. No. 6,491,726 produces such rearward motion. Where a viable posterior ligament is present one can use this ligament to generate this posterior motion of the femur on the tibia (rollback).

A knee device that allows anterior-posterior motion of the femur on the tibia can allow maximum passive flexion even in the absence of a competent posterior cruciate ligament. As the leg is forced into maximum passive flexion the proximal tibia will be forced forward by pivoting on the impinging proximal, posterior tibial soft tissue if the prosthetic knee allows anterior motion of the proximal tibia: The absence of a competent posterior ligament, coupled with a device that permits anterior-posterior motion of the femur on the tibia, unfortunately, results in anterior-posterior instability of the knee. If this motion is unconstrained, except by the action of functioning ligaments, then the instability is likewise unconstrained and is undesirable.

The position of the tibia during maximum passive flexion activities typically requires substantial axial rotation of the tibia relative to the femur. This rotation (approximately 25°) may be sufficient to produce placement of one of the posterior femoral condyles to be anterior to the posterior edge of its corresponding tibial condyle. That is, the femoral condyle may overhang the tibia on one side. Thus a knee replacement should also allow such rotation, but preferably without overhang. A device where the bearing can rotate on the tibial component is ideal for such a situation.

The prosthesis shown in U.S. Pat. No. 5,702,466 can be used for a knee device to exploit the ability of the posterior cruciate ligament to produce rollback and to provide anterior-posterior translation and axial rotation needed to obtain maximum passive flexion. Unfortunately there have been some problems experienced with this design in clinical use. Anterior knee pain, particularly on flexion, is one of these problems. This probably results from an incompetent posterior cruciate ligament producing anterior motion of the femur on the tibia rather than rollback. This anterior motion will produce impingement between the anterior aspect of the bearing and soft tissue structures of the knee. Such impingement can produce such pain. This incompetence is quite common and is the reason that anterior motion of the femur relative to the tibia is commonly observed with knee designs that allow such motion.

A posterior stabilized knee, as shown in U.S. Pat. No. 6,475,241 or U.S. Pat. No. 6,491,726 is preferred for those situations where a competent posterior ligament is not present. More particularly, the designs shown in U.S. Pat. No. 6,475,241 and U.S. Pat. No. 6,491,726 reliably produce needed rollback and provided needed axial bearing rotation. Further, these designs limit anterior-posterior instability to essentially normal limits. Where there is a competent posterior cruciate ligament a prosthetic device of the type shown in U.S. Pat. No. 5,702,466 seems preferable since it allows the natural structures to provide such action rather than the mechanical structures of the posterior stabilized device.

The problem however is that the identification of a viable cruciate ligament is not easily accomplished by many surgeons and a once competent ligament may become incompetent. Thus it is desirable to improve the performance of the prosthesis shown in U.S. Pat. No. 5,702,466 in the presence of an incompetent posterior cruciate ligament.

FIGS. 11–13 of U.S. Pat. No. 5,702,466 show an embodiment where the arm of the control arm assembly is formed with a channel and where the bearing includes a shoulder engaged in the channel. The channel and the shoulder function to limit anterior movement of the bearing relative to the control arm and the tibial component and, hence, enhance stability in those situations where there is not a viable cruciate ligament or where the ligament becomes incompetent after implantation of the prosthesis. However, the interengageable channel and shoulder complicate implantation of the prosthesis and complicate removal of the prosthesis that may be required intraoperatively or during revision surgery.

Surgery to implant the prosthetic device shown in FIGS. 11–13 of U.S. Pat. No. 5,702,466 typically is completed by resecting the superior end of the tibia and the inferior end of the femur. The resected ends of the tibia and femur may be prepared further by forming cavities. The stem of the tibial component then is inserted into the cavity formed in the resected superior end of the tibia so that the platform of the tibial component is supported on the resected end of the tibia. The bearing then is assembled with the control arm and the cone that projects from the control arm is inserted into the conical recess in the tibial component. The femoral component then is mounted to the resected inferior surface of the femur. This sequence is required because the subassembly of the control arm and the bearing cannot be mounted easily into the conical recess of the tibial component once the femoral component has been mounted to the femur.

Revision surgery occasionally is necessary. One possible reason for revision surgery would be to replace a defective bearing. In this situation, the femoral component is likely to be properly implanted and perfectly functional. The presence of the properly implanted femoral component significantly complicates the revision surgery, particularly during the implantation of the new bearing and control arm assembly. This implantation is particularly impeded for those prostheses where the control arm assembly is formed with a channel and where the bearing includes a shoulder to engage the channel as depicted in FIGS. 11–13 of U.S. Pat. No. 5,702,466. Surgeons may try to retract the joint sufficiently so that the cone of the bearing/control arm subassembly can be inserted into the recess of the tibial component. However, such excessive retraction of the joint can stretch ligaments and complicate post-surgery recovery. In other instances, the surgeon may remove a properly implanted and perfectly functional femoral component so that the components of the prosthesis can be implanted during revision surgery in the same sequence employed during the initial surgery to implant the prosthesis. The femoral component often is secured in place by adhesive, bone tissue or some combination thereof. Hence, the removal of the properly implanted femoral component can damage the femur and contribute to post-surgery trauma for the patient.

The presence of the properly implanted femoral component also can complicate the removal of the bearing and control arm assembly during revision surgery for those instances where the arm of the control arm assembly is formed with a channel and where the bearing includes a shoulder engaged in the channel. In particular, the control arm must be removed with the bearing. However, the cone of the control arm is trapped in the recess of the tibial component. Problems of removing the bearing during revision surgery are less severe than problems relating to the implantation of a new bearing during revision surgery. In particular, the previously implanted bearing can be broken by the surgeon and removed in pieces. This solution is not ideal, but may be acceptable during the bearing-removal phase of revision surgery. However, this option is not available to implant a new bearing because the preferred new bearing is of unitary construction.

The physical condition of the patient often will have changed between the time of the implantation of the original prosthesis and the time of the revision surgery. In some situations, the deterioration of the joint may be the reason for the revision surgery. More particularly, the patient may have been in a physical condition to justify the implantation of a prosthetic joint that permits anterior/posterior sliding movement of the bearing on the tibial component when the initial prosthesis was implanted. However, the condition of the patient may have changed so that the added mobility provided by the anterior/posterior sliding movement of the bearing is no longer appropriate. Rather, the patient may require a prosthetic joint that permits rotational movement of the bearing on the tibial component without anterior/posterior sliding movement. In other situations, it may be necessary to provide only limited rotational movement of the bearing on the tibial component with no anterior/posterior sliding movement of the bearing. These changed conditions of the patient have required the surgeon to remove a securely implanted tibial component and to implant a new tibial component consistent with the changed physical characteristics of the patient. Such an extensive revision surgery is traumatic for any patient, and particularly for an elderly patient suffering from problems attributable to reduced mobility.

The subject invention was developed in view of these problems encountered during revision surgery. An object of the invention is to facilitate proper positioning of a bearing/control arm subassembly during revision surgery and particularly for those prosthetic joints that have structure for limiting anterior movement of the bearing relative to the control arm. Another object of the invention is to provide a prosthetic joint that can match the mobility needs of the patient, particularly during revision surgery.

SUMMARY OF THE INVENTION

The invention relates to a knee prosthesis that has a femoral component having a superior surface for mounting to the resected inferior or distal end of a femur. The femoral component also has an inferior articular bearing surface with medial and lateral convex condyles. The knee joint prosthesis also includes a tibial component with an inferior face configured for mounting to the superior or proximal end of a resected tibia. The tibial component also has a superior bearing face. A bearing is disposed between the femoral and tibial components. The bearing includes an inferior bearing surface disposed in rotational and sliding bearing relationship with the superior surface of the tibial component. The bearing further includes a superior surface with concave condyles disposed in articular bearing engagement with the condyles of the femoral component. The concave superior surface of the bearing may be configured to provide surface contact with the condyles of the femoral component at full extension of the knee. However, the concave superior surface of the bearing is incongruent with the condyles of the femoral component during flexion, and achieves only line contact. The incongruency contributes to the generation of roll back during flexion, and hence contributes to anterior-posterior sliding movement of the bearing relative to the tibial component during flexion.

The knee joint prosthesis further includes a control arm assembly. The control arm assembly is rotatably engaged with the femoral component and is slidably engaged with the inferior surface of the bearing. More particularly, the inferior surface of the bearing may include anterior-posterior groove that slidably engages the control arm. Anterior portions of the control arm are formed with a control arm stop pin that engage in a recess in the inferior surface of the bearing for limiting the amount of anterior sliding movement of the bearing on the tibial component and the control arm assembly. The engagement of the bearing with the control arm stop pin reduces or avoids possible impingement of the prosthesis with anterior knee tissues, thereby reducing anterior knee pain. The control arm stop pin preferably is removably mounted to the anterior end of the control arm. More particularly, the control arm stop pin preferably comprises attachment means for removable attachment of the control arm stop pin to anterior portions of the control arm. The attachment means preferably is accessible from anterior portions of the assembled prosthesis.

The above-described control arm stop pin removably mounted to anterior portions of the control arm limit anterior movement of the bearing relative to the control arm, and hence relative to the tibial component. However, posterior sliding movement of the bearing on the tibial component is permitted. Some instances will occur during revision surgery where it is desired to limit mobility of the patient due to changed conditions of the patient between the initial implantation of the bearing and a revision surgery. In these situations, it may be desirable to provide a prosthetic joint that permits the bearing to rotate on the tibial platform without permitting anterior/posterior sliding movement. This initially reduced mobility can be achieved without replacing either the tibial or femoral components. More particularly, the control arm can be provided with a posterior control arm stop pin at a posterior portion of the control arm. The posterior control arm stop pin may be formed integrally or unitarily with the control arm or may be attached removably to the control arm. The original tibial component and femoral component may remain implanted during the revision surgery. The pivotal support of a control arm assembly that has posterior control arm stop pin then may be mounted at the superior surface of the tibial component. At this point, the removable anterior control arm stop pin will not yet be in place.

The bearing in this embodiment includes a groove for accommodating the control arm and further includes notches that extend in a superior direction at both the anterior and posterior ends of the groove. The bearing is implanted by sliding the groove in an anterior-to-posterior direction along the control arm so that the inferior surface of the bearing is slidably engaged on the superior surface of the tibial component. The anterior-to-posterior sliding movement of the bearing stops when the posterior control arm stop pin engages the notch at the posterior end of the groove. The anterior control arm stop pin then is mounted to the anterior portion of the control arm and is nested substantially nested in the anterior notch in the groove of the bearing. As a result, the bearing is trapped between the anterior and posterior control arm stop pins and movement in anterior or posterior directions on the tibial component. However, the bearing can rotate with the control arm on the superior surface of the tibial component is restricted.

In some situations it may be desired to limit the amount of rotational movement of the bearing on the tibial component. For these situations, the bearing may include a rotation-limiting recess formed in the inferior surface of the bearing and at the anterior extreme of the bearing. The rotation-limiting recess may be dimensioned to limit rotation of the bearing by approximately 15° in either direction. The prosthetic joint then may include a rotational stop pin mounted substantially at the anterior extreme of the tibial component and in a position to engage in the rotation-limiting recess of the bearing. The rotation-limiting stop pin may include a support that can be implanted in the tibia anteriorly of the tibial component. The rotation-limiting stop pin then can be mounted in the support and may project sufficiently from the superior surface of the tibial component to engage in the rotation-limiting recess of the bearing.

DETAILED DESCRIPTION OF THE PREFERRED EMBODIMENTS

Figure 1:
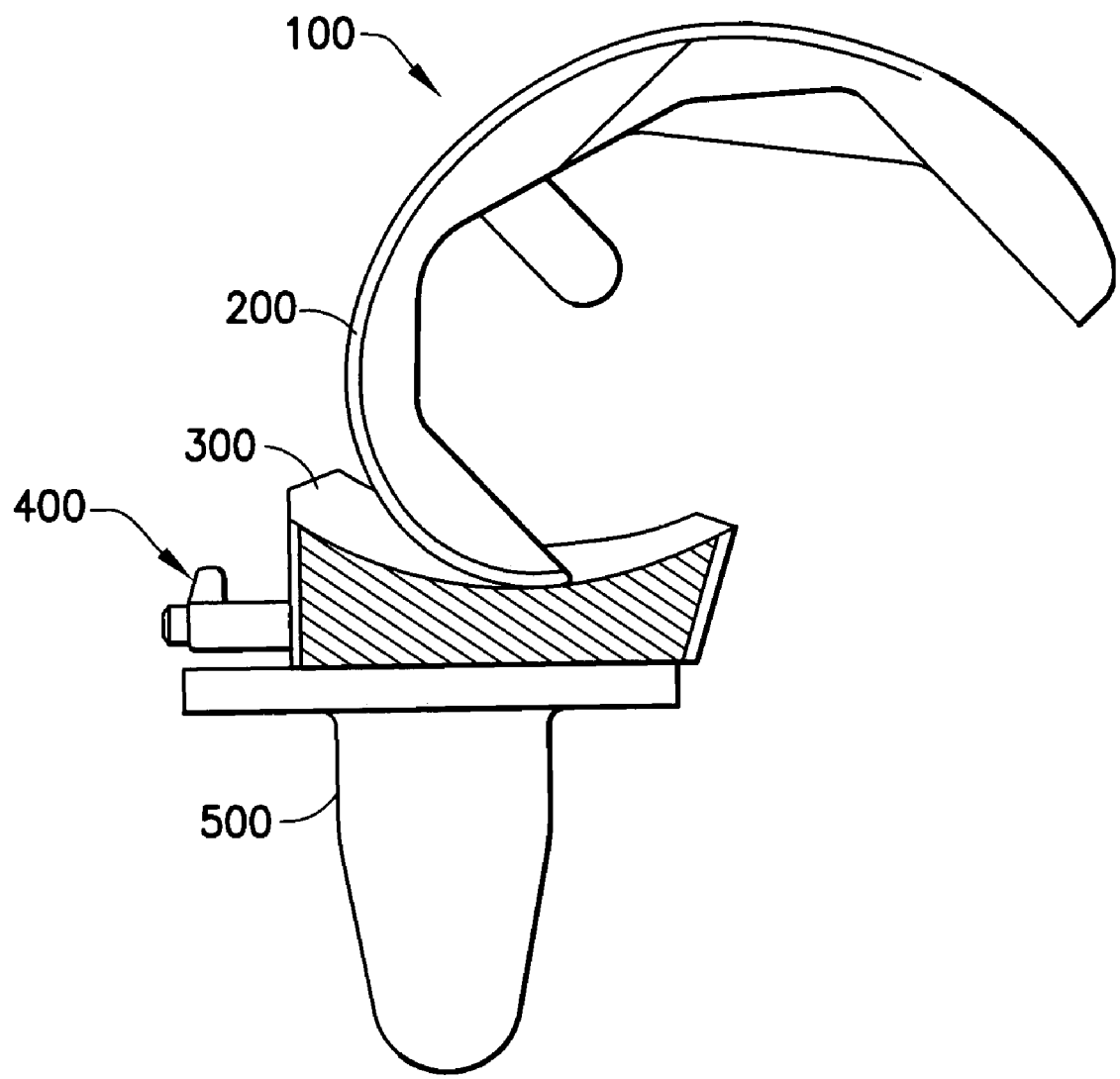
FIG. 1 is a side elevational view, partly in section, showing a knee joint prosthesis in accordance with the subject invention.

A prosthetic knee device in accordance with the invention is identified by the numeral 100 and is shown in FIG. 1, at 162° of flexion. This is the maximum human passive flexion even in Asian cultures where deep squatting and sitting on the floor is common. During such flexion the tibia, and thus the tibial component 500, move forward relative to the femur and the bearing 300 moves backward on the tibial component as shown. Such motion is necessary to achieve flexion of this magnitude.

The prosthetic knee device 100 comprises a femoral component 200, bearing 300, control arm 400 and a tibial component 500. The femoral and tibial components 200 and 500 respectively are identical to the femoral and tibial components in prior art LCS prosthetic knees.

Figure 2:
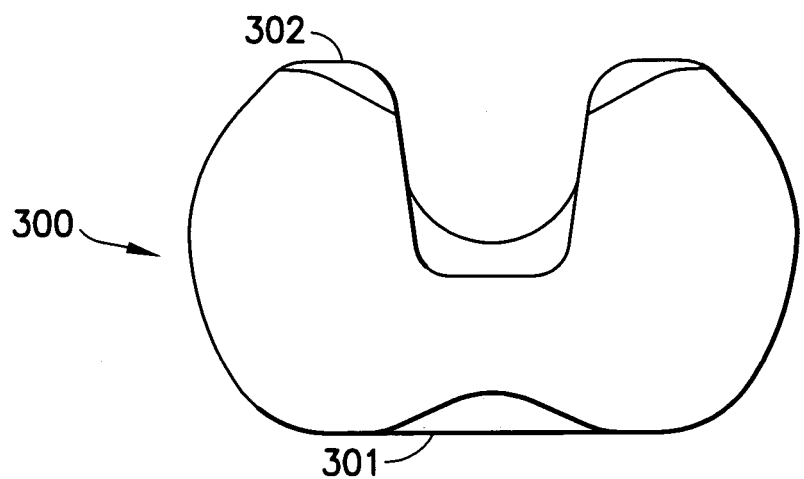
FIG. 2 is a top plan view of the bearing shown in FIG. 1.
Figure 3:
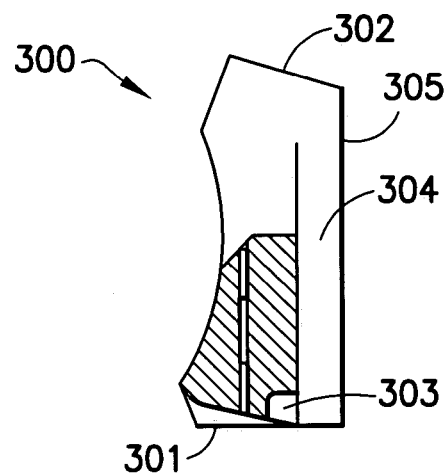
FIG. 3 is a side elevational view, partly in section, of the bearing.
Figure 4:
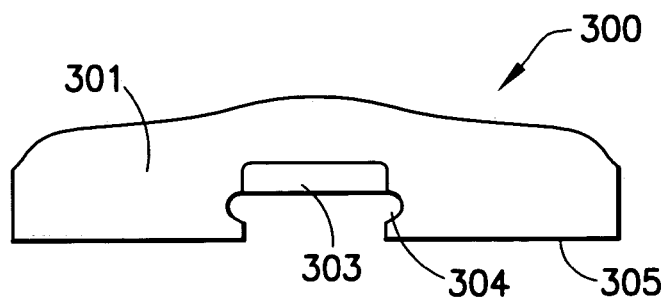
FIG. 4 is a front elevational view of the bearing.

The bearing 300 is shown in FIGS. 2–4. More particularly, the bearing 300 is formed from an ultra high molecular weight polyethylene and is similar to the earlier Flexglide bearing except the distance from its anterior surface 301 to its posterior surface 302 is somewhat less than the earlier design so as to reduce the potential for tissue impingement on deep flexion. The added width of the earlier bearing was an overreaction to the problem of spinout of the original rotating platform bearing. The original Flexglide bearing has the same plan form as the rotating platform bearing modified to improve resistance to spinout. Spinout is, however, not a problem with the Flexglide bearing and this increased width is not necessary. The bearing 300 also contains a stop recess 303 at an anterior and inferior extreme position on the bearing and a dovetail groove 304 that extends along the inferior surface 305 of the bearing from the anterior extreme to the posterior extreme. Anterior portions of the dovetail grove 304 align with the recess 303.

Figure 5:
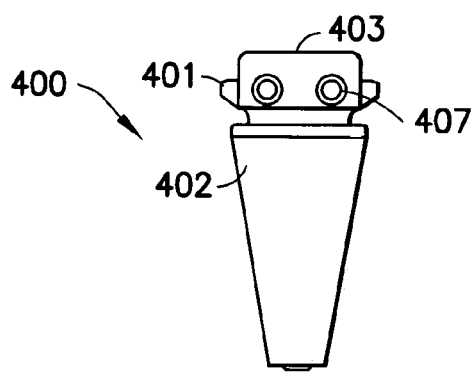
FIG. 5 is a front elevational view of the control arm assembly.
Figure 6B:
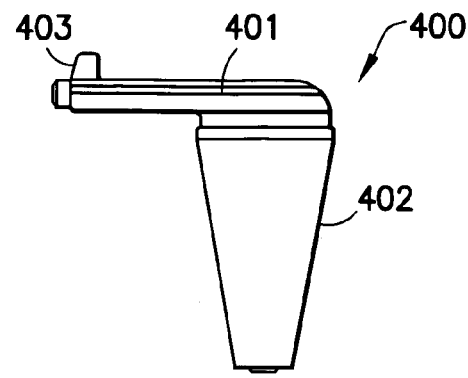
FIG. 6B is a side elevational view of the control arm assembly in its assembled condition.
Figure 6A:
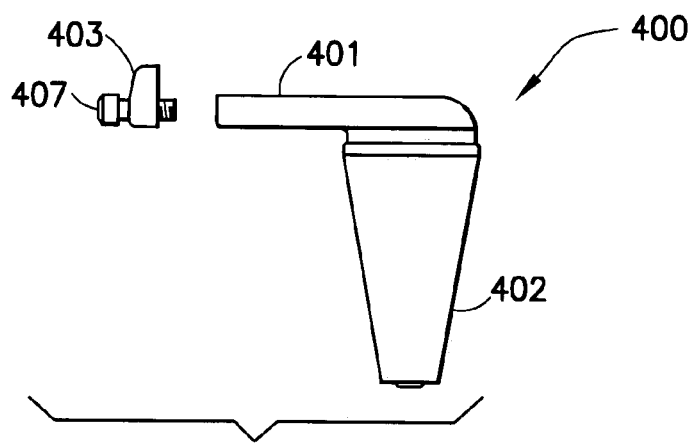
FIG. 6A is an exploded side elevational View of the control arm assembly.
Figure 7A:
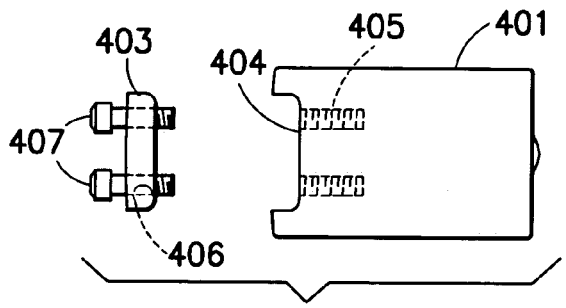
FIG. 7A is an exploded top plan view of the control arm assembly.
Figure 7B:
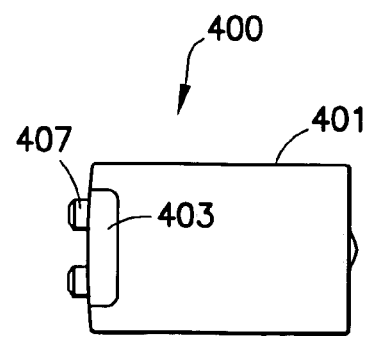
FIG. 7B is a top plan view of the control arm assembly in its assembled condition.

The control arm assembly 400 shown in FIGS. 5–7 is similar to that of U.S. Pat. No. 5,702,466 except that the dovetail-shaped arm 401 is wider to provide additional stability of the control arm assembly 400. This stability is desirable since the cone 402 of this design is smaller than that of the original for the larger size knees. The control arm assembly 400 also contains a removable anterior stop 403 removably mounted to anterior portions of the control arm 401. More particularly, the control arm 401 is formed with an anterior notch 404 and two threaded apertures 405 extending posteriorly into the anterior notch 404. The stop 403 is configured to fit closely in the notch 404. Both the control arm 401 and the stop 403 are formed from a metallic material. An exemplary stop 403 according to the present disclosure is formed with two apertures 406 extending therethrough and disposed to align with the threaded apertures 405 in the notch 404 when the stop 403 is mounted in the notch 404. The exemplary stop 403 further includes two screws 407 rotatably trapped in the apertures 406 of the stop 403. The screws 407 are dimensioned for threaded engagement in the threaded apertures 405 of the control arm 401. Thus, the screws 407 can be used to removably mount the stop 403 to the anterior end of the control arm 400, and function as attachment means according to the present disclosure. Alternative attachment means which function to removably secure the stop are contemplated. As shown in FIG. 6B, the stop 403 is dimensioned to extend superiorly from anterior portions of the control arm 400 and is configured for engagement in the stop recess in the bearing 300. Alternate stop designs/configurations are contemplated according to the present disclosure, provided such stop design/configuration may be removably mounted relative to the control arm and functions to limit anterior movement of the bearing.

The tibial component includes a projection 501 configured for mounting in a recess prepared in the proximal end of the resected tibia. The tibial component 500 further includes a platform 502 with a substantially planar superior bearing surface 503 for bearing engagement with the inferior surface 305 of the bearing. A conical recess 504 extends through the platform 502 and into the projection 501. The conical recess is configured for rotational and/or pivotal relative motion receiving the cone 402 of the control arm assembly 400, e.g., through rotational and/or pivotal relative motion.

Figure 11:
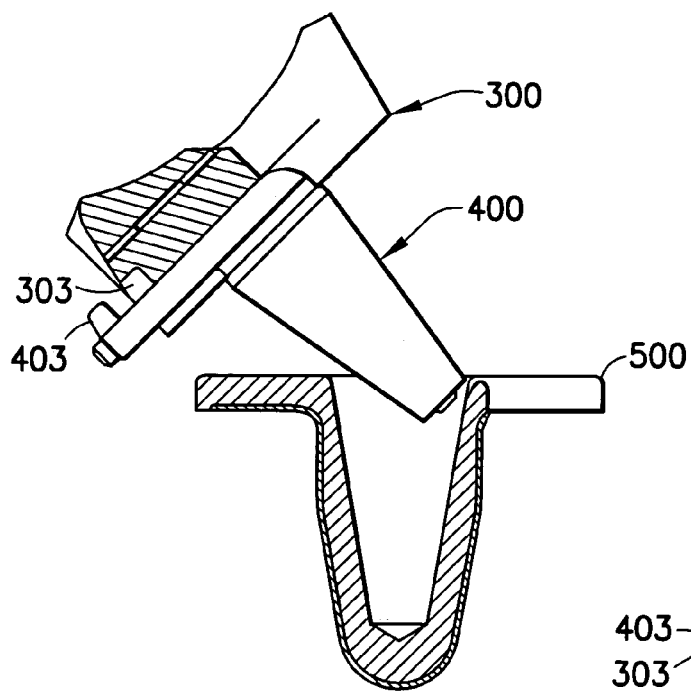
FIG. 11 is a cross-sectional view of the bearing and the control arm being assembled with the tibial component.

The bearing 300 is assembled on to the control arm 400 by sliding the dovetail groove 304 onto the dovetail 401. The assembly is then inserted into the tibial component 500 in the usual fashion as shown in FIG. 11.

In flexion the femoral component 200 will roll backward on the tibial component 500. The bearing 300 moves backward with the femoral component and thus will slide on the dovetailed connection backward on the control arm 400 as shown in FIG. 1.

Figure 12:
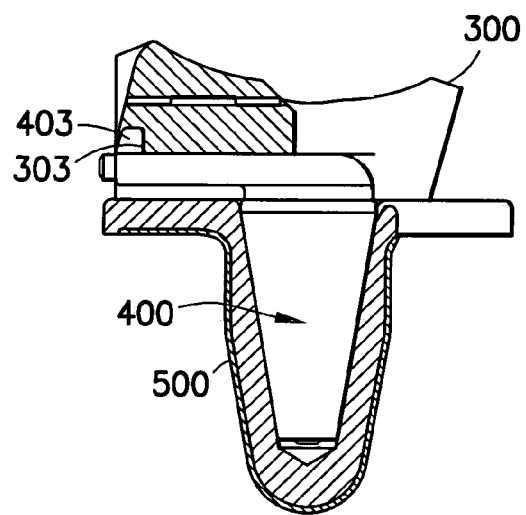
FIG. 12 is a cross-sectional view of the bearing and control arm fully assembled into the tibial component.
Figure 13:
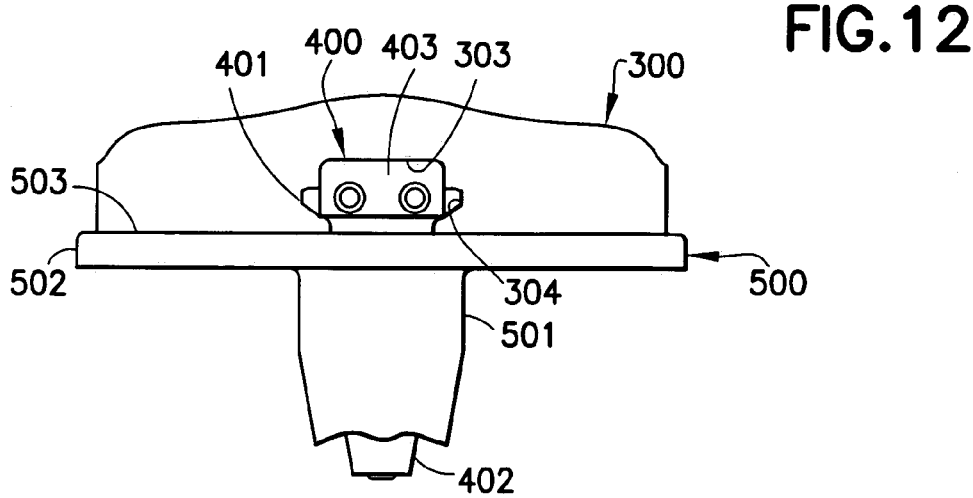
FIG. 13 is a front elevational view of the assembled components of FIG. 12.
Figure 14:
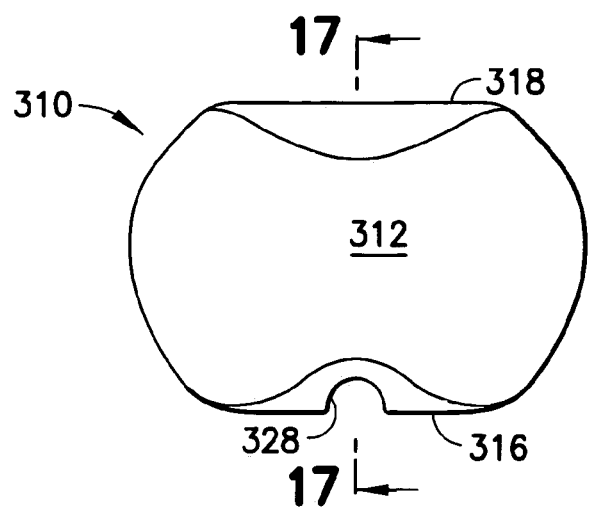
FIG. 14 is a top plan view of a bearing in accordance with an alternate embodiment of the invention.
Figure 15:
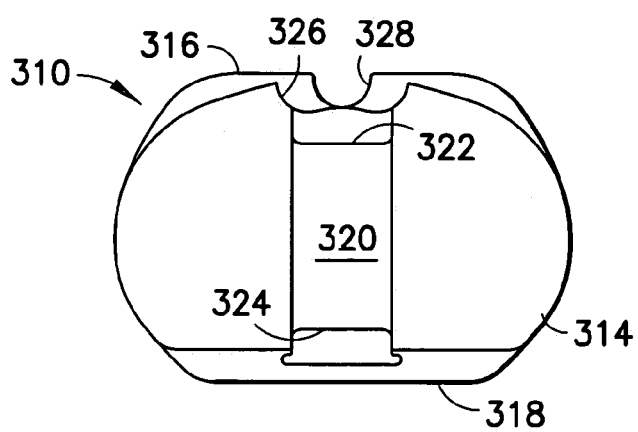
FIG. 15 is a bottom plan view of the bearing shown in FIG. 14.
Figure 16:
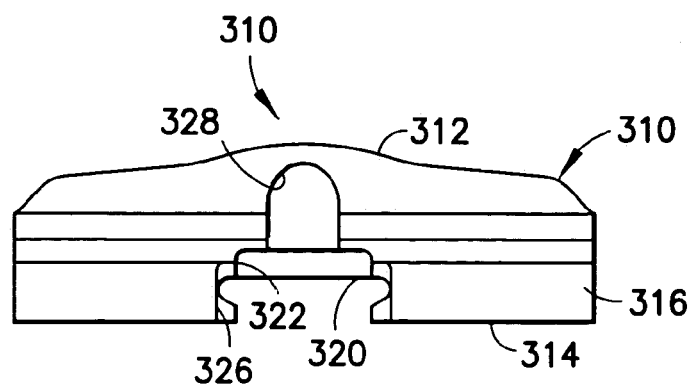
FIG. 16 is a front elevational view of the bearing shown in FIG. 14.
Figure 17:
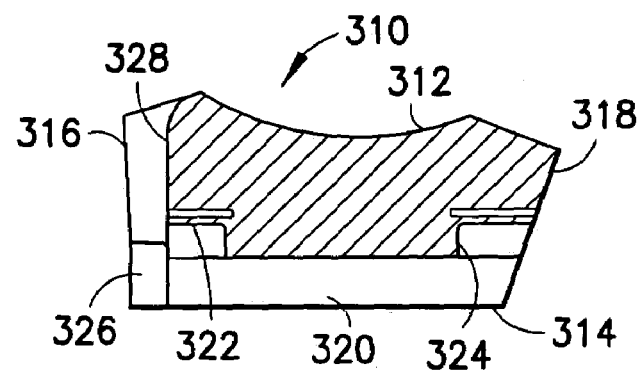
FIG. 17 is a cross-sectional view taken along line 17—17 in FIG. 14.

During extension the femoral component 200 will roll forward on the tibial component 500. Thus the bearing 300 will also move forward to the position shown in FIG. 12. The stop 403 prevents additional forward motion beyond this point. Such additional motion may result from a lax posterior cruciate ligament, or other reason. This reduces possible impingement with anterior knee tissues thereby reducing anterior knee pain. It also reduces anterior-posterior laxity of the knee.

Revision surgery occasionally is necessary. As noted above, such revision surgery with prior art prostheses could require removal of a properly implanted femoral component merely to disassemble the prosthetic joint and to replace, for example, a defective bearing. With the subject invention, however, it is unnecessary to remove a properly implanted femoral component. Rather, the femoral component can remain in place and disassembly during revision surgery can be achieved easily merely by removing the stop 403. Such removal can be achieved by unthreading the screws 407 which are accessible from anterior portions of the prosthetic component. Implantation of a new bearing can be achieved easily with the femoral component in place by retracting the joint sufficiently to allow the posterior lip of the bearing to clear the condyles of the femoral component.

Figure 25:
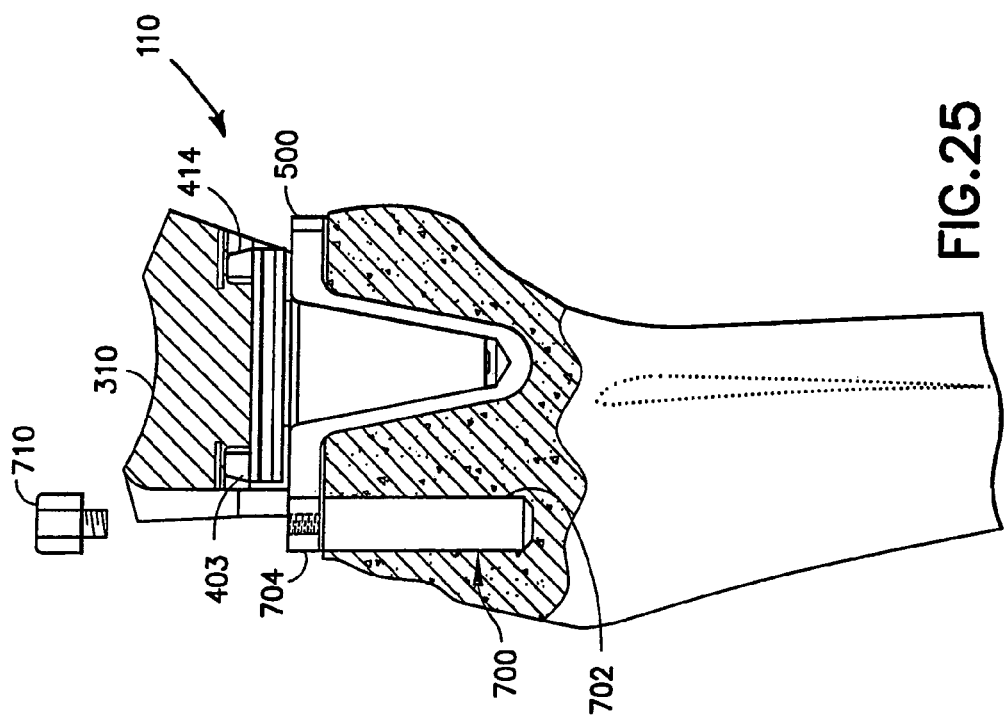
FIG. 25 is an exploded schematic view after mounting of the bearing and the control arm assembly and during implantation of the rotation-limiting stop pin.
Figure 24:
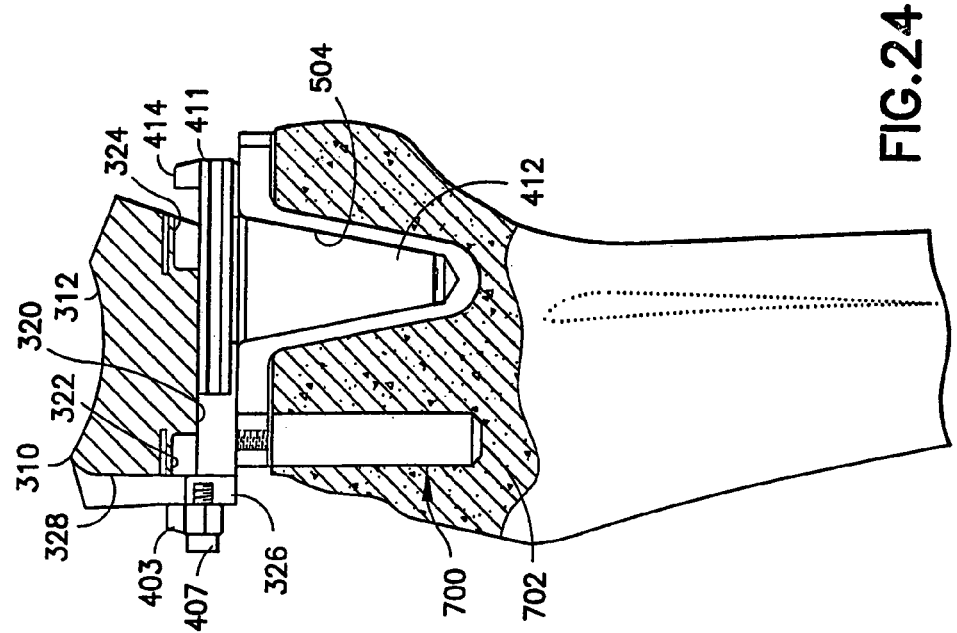
FIG. 24 is an exploded side elevational view schematically showing the implantation of the bearing and the anterior control arm stop pin.

An alternate prosthetic joint in accordance with the invention is illustrated in FIGS. 14–25 and is identified generally by the numeral 110 in FIG. 25. The alternate prosthetic joint 110 includes a femoral component 200 identical to the femoral component described and illustrated with respect to the first embodiment. Additionally, the alternate prosthetic joint 110 includes a tibial component 500 identical to the tibial component described and illustrated with respect to the first component. In this regard, the alternate prosthetic joint 110 may be assembled during revision surgery without replacing a previously implanted femoral component 200 and tibial component 500.

Figure 8:
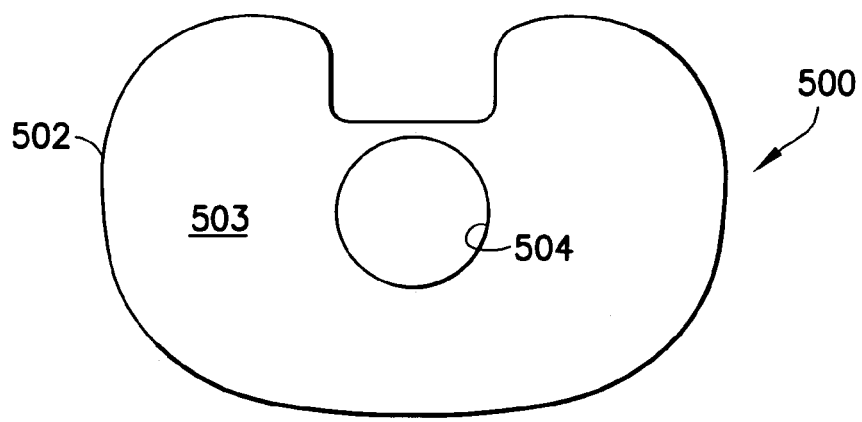
FIG. 8 is a top plan view of the tibial component.
Figure 9:
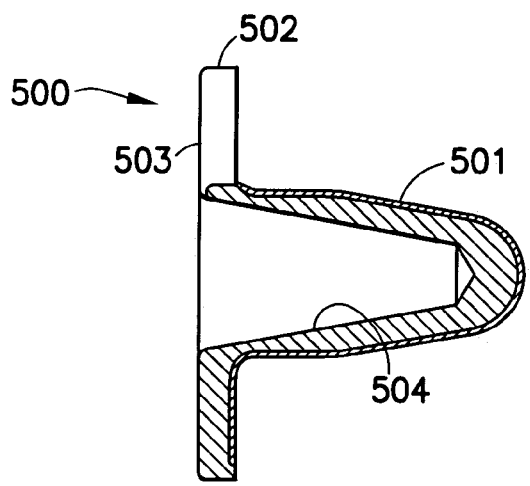
FIG. 9 is a cross-sectional view of the tibial component taken along an anterior-posterior plane.
Figure 10:
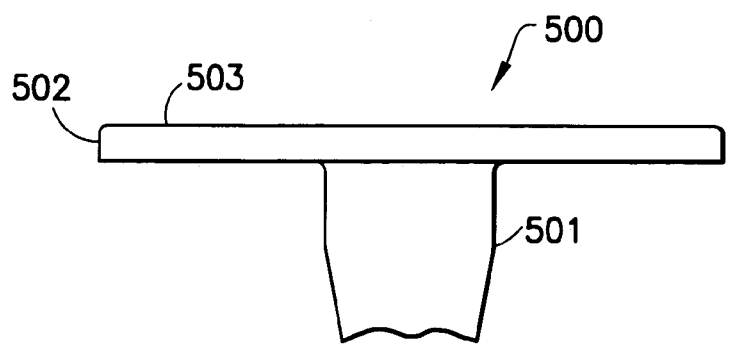
FIG. 10 is a front elevational view of the tibial component.

The alternate prosthetic joint 110 include a bearing 310 that differs from the bearing 300 described with respect to the first embodiment. More particularly, as shown in FIGS. 14–17, the bearing 310 includes a superior surface 312 formed with two concave condylar bearing surfaces for receiving the convex condyles of the femoral component 200. The bearing 310 further includes an inferior bearing surface 314 for limited rotational bearing engagement on the superior bearing surface 503 of the tibial component 500 as illustrated in FIGS. 8–10 above. The bearing 310 further includes an anterior extreme 316 and a posterior extreme 318. A dovetailed groove 320 is formed into the inferior surface 314 of the bearing 310 and extends from the anterior extreme 316 to the posterior extreme 318. Portions of the groove 320 near the anterior extreme 316 are characterized by an anterior notch 322 that opens to the anterior extreme 316 and that extends deeper into the groove 320 and hence more in a superior direction. Similarly, portions of the groove 320 adjacent the posterior extreme 318 define a posterior notch 324 that opens to the posterior extreme 318 and that extends more in a superior direction than adjacent portions of the groove 320.

The bearing 310 further includes the rotation-limiting recess 326 that opens to the inferior surface 314 and to the anterior extreme 316. The rotation-limiting recess 326 is substantially symmetrical with the anterior/posterior centerline of the bearing, and hence is substantially symmetrical with the groove 320. However, the recess 326 extends through a medial/lateral arc to approximately 15° from either side of the anterior/posterior centerline. Central portions of the recess 326 also open to the superior surface of the bearing 312 adjacent the anterior extreme to define a generally semi-circular notch 328 in a central position on the anterior extreme 316 and extending completely from the superior surface 312 to the inferior surface 314. The semi-circular notch 328 permits access by a screwdriver or similar tool for implanting a rotation-limiting stop pin as explained further herein.

Figure 18:
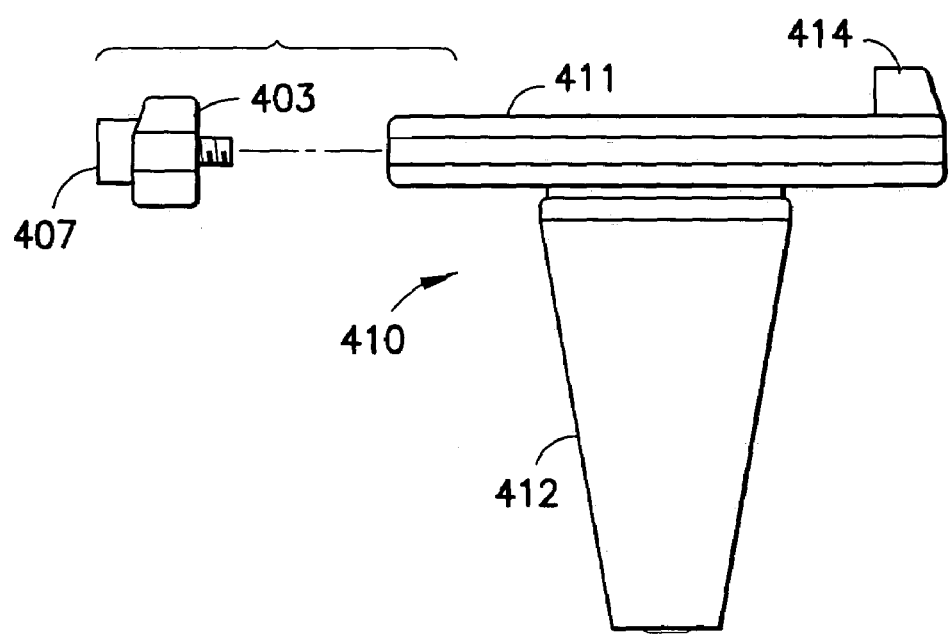
FIG. 18 is an exploded side elevational view of a control arm assembly in accordance with the second embodiment of the invention.

The alternate prosthetic joint 110 further includes a control arm assembly 410 as shown in FIG. 18. The control arm assembly 410 includes a control arm 411 and a cone 412 that are similar to the control arm 401 and the cone 402 of the first embodiment. However, the control arm 410 is formed unitarily with a posterior control arm stop pin 414 projecting up at the posterior end of the control arm 411. The anterior extreme of the control arm 411 is formed with an anterior notch substantially identical to the notch 404 shown in FIG. 7A and the anterior notch is provided with threaded apertures identical to the threaded apertures 405 shown in FIG. 7A. The control arm assembly 410 further includes a removable anterior control arm stop 403 identical to the control arm stop 403 shown in FIGS. 5–7B. The anterior control arm stop pin 403 can be attached removably to the anterior notch in the control arm 411 by screws 407 that can be engaged threadedly in the threaded apertures in the anterior extreme of the control arm 411.

Figure 19:
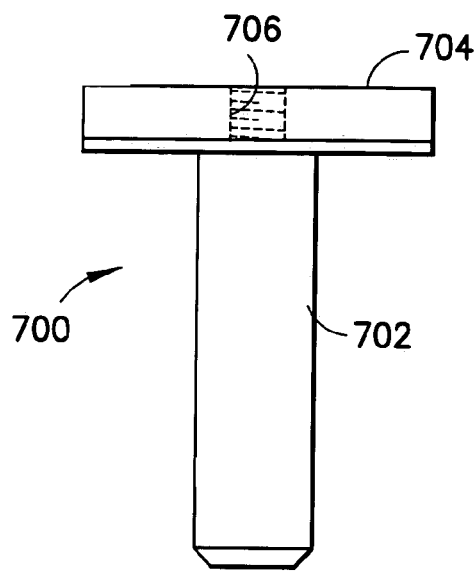
FIG. 19 is a front elevational view of a rotation-limiting stop pin support for optional use in the second embodiment.
Figure 20:
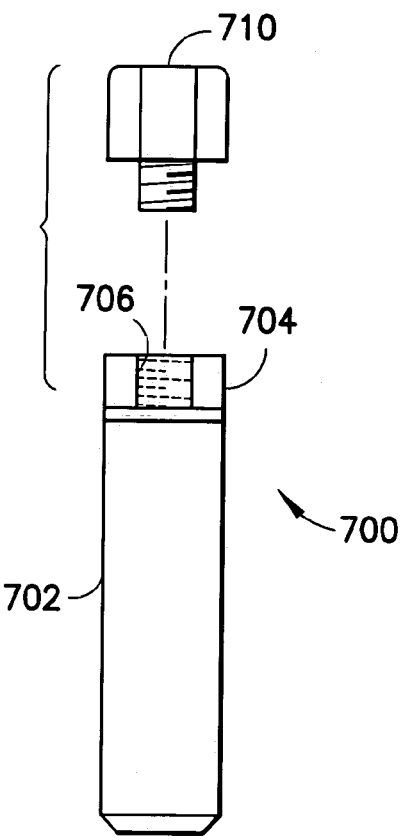
FIG. 20 is an exploded side elevational view of the rotation-limiting stop pin support and the rotation-limiting stop pin.
Figure 23:
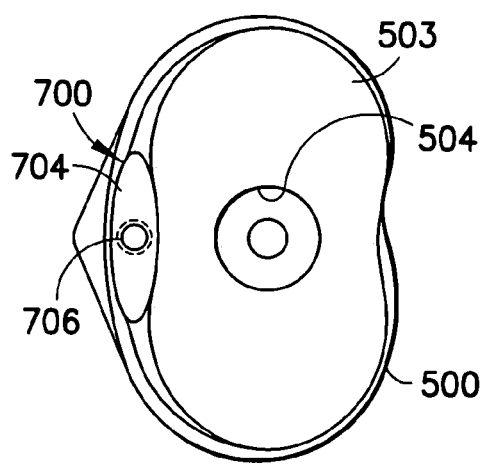
FIG. 23 is a top plan view showing the implanted tibial component and the implanted rotation-limiting stop pin support.

The prosthetic joint 110 optionally is provided with a stop support 700 as shown in FIGS. 19 and 20. The stop support 700 includes a generally cylindrical base 702 and a platform 704. The platform 704 is formed with a threaded aperture 706 extending down into a top surface of the platform 704, and hence in a superior-to-inferior direction. The stop platform 704 is configured for substantially nesting with the anterior extreme of the tibial component 500. Exterior surface regions of the base 702 and inferior surface regions of the platform 704 may be formed with a bone ingrowth surface provided by roughening or by the application of a porous material. The superior surface of the platform 704 is dimensioned to lie substantially flush with the superior surface 503 of the tibial component 500 or slightly recessed from the superior surface 503. The stop pin support 700 is used with a rotation-limiting stop pin 710 that can be engaged threadedly in the threaded aperture 706.

Figure 21:
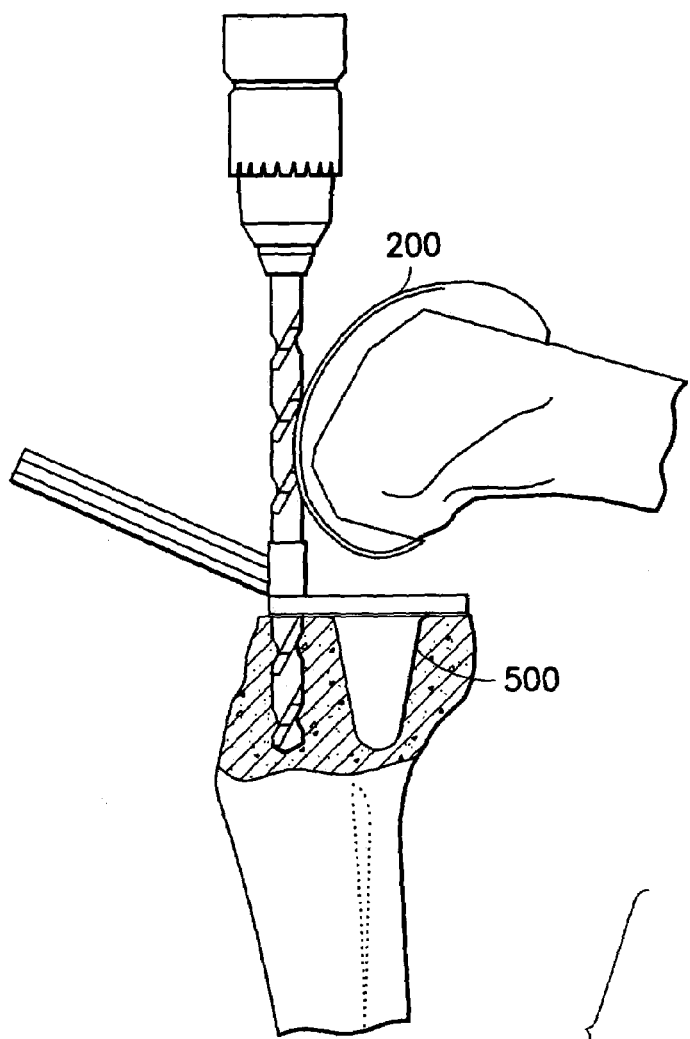
FIG. 21 is a schematic view showing preparation of a tibia for implantation of the rotation-limiting stop pin support during revision surgery.
Figure 22:
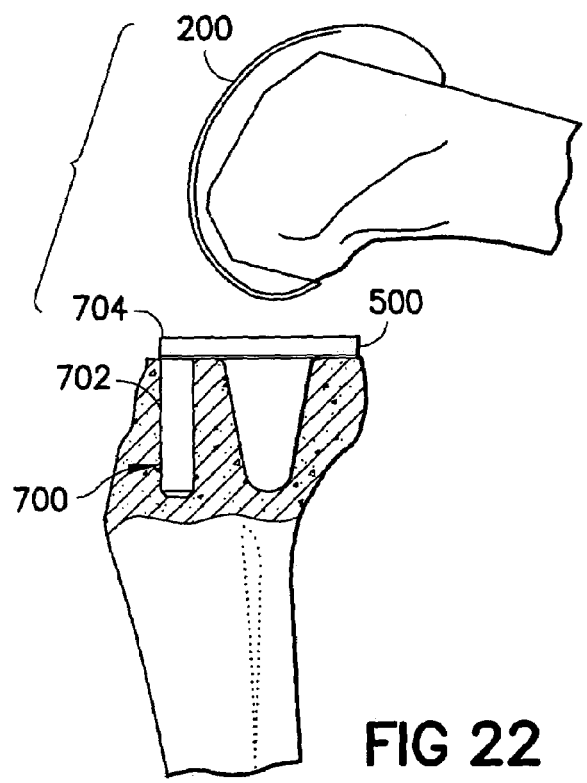
FIG. 22 is a schematic view showing the fully implanted rotation-limiting stop pin support.

FIGS. 21–25 illustrate use of the alternate prosthetic joint 110 during revision surgery. Thus, in the illustrated example, the femoral component 200 and the tibial component 500 from a prior implantation of a prosthetic joint remain in place. FIG. 21 shows preparation of the tibia for the optional use of the rotation-limiting stop pin 710. In particular, a hole is drilled downwardly into the resected proximal end of the tibia at a position adjacent to and anteriorly of the tibial component 500 and at a position substantially centrally disposed between medial and lateral extremes of the tibial component 500. The base 702 of the stop pin support 700 then is implanted into the prepared hole. As a result, the superior surface of the platform 704 is substantially flush with the superior surface 503 of the tibial platform 502. Additionally, the threaded aperture 706 of the platform 704 is substantially symmetrically aligned relative to the medial and lateral extremes of the tibial platform 502. The cone 412 of the control arm assembly 400 then is positioned rotatably in the recess 504 of the tibial component 500 so that the posterior control arm stop pin 414 is near the posterior extreme of the tibial platform 502. The bearing 310 then is mounted to the assembled tibial component 500 and control arm 411. In particular, the dovetailed groove 320 of the bearing 310 is slid onto the control arm 411 in an anterior-to-posterior direction. This sliding movement of the bearing 310 in a posterior direction ends when the posterior control arm stop pin 414 nests in the posterior notch 324 of the bearing 310. The anterior stop pin 403 then is mounted to the anterior extreme of the control arm 411 substantially as described with respect to the first embodiment. In particular, the screws 407 are engaged threadedly in the threaded apertures in the anterior end of the control arm 411. As a result, the bearing is trapped between the anterior and posterior control arm stop pins 403 and 414 as shown in FIG. 25. At this point, the prosthetic joint 110 would prevent anterior/posterior sliding movement of the bearing 310 on the tibial platform 502, but would permit rotational movement of the bearing 310 on the tibial platform 502. This level of mobility is less than the level of mobility provided by the first embodiment, but may be appropriate for many revision surgeries.

In some situations, it is desirably and necessary to further restrict mobility of the prosthetic joint. In these situations the optional rotation-limiting stop pin 710 may be employed. In particular, the stop pin is moved in an inferior direction through the notch 328 in the bearing 310 and is engaged threadedly in the threaded aperture 706 in the stop platform 704, as shown schematically in FIG. 25. The rotation-limiting stop pin 710 permits the bearing to rotate approximately 15° in either direction within the rotation-limiting recess 326. However, the recess 326 limits rotation beyond approximately 15° in either direction.

While exemplary prostheses have been described with respect to various specific embodiments, those of ordinary skill in the art will readily appreciate that various modifications, changes and enhancements may be made thereto without departing from the spirit and scope of the present disclosure.

What is claimed is:

1. A prosthetic device comprising:
a first component having a first bearing surface;
a second component having a second bearing surface disposed in sliding bearing engagement with the first bearing surface, the second bearing surface including a groove with opposite first and second ends, first and second notches formed respectively at the first and second ends of said groove; and
a control assembly having a pivotal support pivotally engaged with said first component, a control arm in proximity to the pivotal support, the control arm having opposite first and second ends and being engaged in said groove, a first stop disposed at the first end of the control arm and engageable in the first notch of the bearing and a second stop removably mounted to second end of said control arm by mounting means accessible at said second end of said control arm and being engageable in said second notch, said first and second stops cooperating with said first and second notches for limiting movement of said second component relative to said first component in directions parallel to the control arm.

2. The prosthetic device of claim 1, further comprising means for limiting rotational movement of the second component relative to the first component.

3. The prosthetic device of claim 1, further comprising a rotation-limiting stop pin secured in proximity to the second component and configured for limiting pivotal movement of the first component relative to the second component.

4. The prosthetic device of claim 3, wherein the rotation-limiting stop pin is dimensioned and configured relative to the second component for limiting rotational movement to approximately 30°.

5. The prosthetic device of claim 1, wherein the second stop is removably mounted to the second end of the control arm by at least one screw accessible at the second end of the control arm.

6. The prosthetic device of claim 1, further comprising a third component in articular bearing engagement with a surface of said first component substantially opposite said first bearing surface, said third component being spaced from said control arm assembly through all ranges of articular bearing engagement of said first and third components.

7. A knee joint prosthesis comprising:
- a tibial component having a superior bearing surface;
- a bearing having an inferior surface in sliding bearing engagement with the superior bearing surface of the tibial component, a groove extending substantially from an anterior extreme to a posterior extreme in the inferior surface of the bearing, anterior and posterior notches formed in the inferior surface of the bearing substantially at anterior and posterior ends of the groove;
- a control arm engaged with the tibial component and slidably engaged in the groove of the bearing;
- a posterior control arm stop extending from the control arm and engageable in the posterior notch of the bearing; and
- an anterior control arm stop removably mounted to the anterior end of the control arm by mounting means accessible at the anterior end of the control arm and engageable in the anterior notch of the bearing, the anterior and posterior control arm stops cooperating with the anterior and posterior notches for limiting anterior and posterior movement of the bearing on the superior bearing surface of the tibial component.

8. The prosthesis of claim 7, further comprising a rotation-limiting stop pin fixed relative to the tibial component and disposed for engaging the bearing for limiting rotational movement of the bearing on the tibial component.

9. The prosthesis of claim 8, wherein the rotation-limiting stop and the bearing are configured for permitting approximately 15° of rotation of the bearing in either direction from a central position.

* * * * *